US010245614B2

(12) United States Patent
Kulinsky et al.

(10) Patent No.: US 10,245,614 B2
(45) Date of Patent: Apr. 2, 2019

(54) IMPRINTER FOR CONFORMAL COATING OF THREE-DIMENSIONAL SURFACES

(71) Applicant: The Regents of the University of California, Oakland, CA (US)

(72) Inventors: Lawrence Kulinsky, Los Angeles, CA (US); Arash Kheradvar, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 496 days.

(21) Appl. No.: 14/937,075

(22) Filed: Nov. 10, 2015

(65) Prior Publication Data

US 2016/0129469 A1    May 12, 2016

Related U.S. Application Data

(60) Provisional application No. 62/078,274, filed on Nov. 11, 2014.

(51) Int. Cl.
| | |
|---|---|
| B05B 7/06 | (2006.01) |
| B05D 1/02 | (2006.01) |
| B05D 3/06 | (2006.01) |
| A61L 27/24 | (2006.01) |
| A61L 27/54 | (2006.01) |
| A61L 27/36 | (2006.01) |
| A61L 27/38 | (2006.01) |

(Continued)

(52) U.S. Cl.
CPC ............ *B05D 1/02* (2013.01); *A61L 27/24* (2013.01); *A61L 27/3633* (2013.01); *A61L 27/38* (2013.01); *A61L 27/54* (2013.01); *B05D 3/067* (2013.01); *A61L 2300/414* (2013.01); *C08G 61/02* (2013.01); *C08G 2261/146* (2013.01); *C08G 2261/3424* (2013.01); *C09D 165/04* (2013.01)

(58) Field of Classification Search
CPC .................... B05B 13/0457; B05C 5/0279
USPC .......................... 118/255, 313, 315
See application file for complete search history.

(56) References Cited

U.S. PATENT DOCUMENTS 5,240,745 A *   8/1993   Yamamoto ............ B05B 12/122
                                              427/236
5,788,775 A *   8/1998   Boriani ............... B05B 13/0463
                                              118/315

(Continued)

OTHER PUBLICATIONS

Kim, T.G. et al. 2010 "Microstructured scaffold coated with hydroxyapatite/collagen nanocomposite multilayer for enhanced osteogenic induction of human mesenchymal stem cells" *J Mater Chem* 20: 8927-8933.

*Primary Examiner* — Cachet I Sellman
(74) *Attorney, Agent, or Firm* — Knobbe, Martens, Olson & Bear, LLP

(57) ABSTRACT

Disclosed is an imprinter device comprising an array of adjacent applicators that are arranged so that longitudinal axes of each of the adjacent applicators are parallel to each other, wherein the applicators are configured to make contact with and conform to a surface of a three dimensional (3D) object. In some embodiments, the applicators move independently of each other with respect to the surface of the object, and wherein the applicators are configured to apply a material over the object while in proximity to the surface of the object. Also disclosed are methods of conformal coating a surface of an object.

24 Claims, 13 Drawing Sheets

(A)

(B)

(51) Int. Cl.
  *C08G 61/02*   (2006.01)
  *C09D 165/04*  (2006.01)

(56) References Cited

U.S. PATENT DOCUMENTS

| | | | | |
|---|---|---|---|---|
| 5,846,464 | A  * | 12/1998 | Hoffman | B23Q 1/035 264/219 |
| 6,457,608 | B1 * | 10/2002 | Riney | B05C 5/0279 222/135 |
| 6,695,923 | B1 * | 2/2004 | Schultz | B05B 13/0431 118/323 |
| 8,561,571 | B2 * | 10/2013 | Shioi | B05B 12/04 118/686 |
| 2004/0262816 | A1 * | 12/2004 | Parks | B29C 43/36 264/500 |
| 2008/0125743 | A1 * | 5/2008 | Yuzhakov | A61M 37/0015 604/506 |
| 2012/0238938 | A1 * | 9/2012 | Herekar | A61F 9/0017 604/20 |

* cited by examiner

IMPRINTER FOR CONFORMAL COATING OF THREE-DIMENSIONAL SURFACES

INCORPORATION BY REFERENCE TO ANY PRIORITY APPLICATIONS

This application claims priority U.S. Provisional Application No. 62/078,274 filed on Nov. 11, 2014. Any and all applications for which a foreign or domestic priority claim is identified in the Application Data Sheet, as filed with the present application, are hereby incorporated by reference under 37 CFR 1.57.

BACKGROUND

It is difficult to produce a conformal coating of complex 3D surfaces. Especially challenging is deposition of a biologically active layer, such as cell-laden collagen, that cannot be sprayed (too much shear stress will damage cells) or brushed across surface (the collagen layer will not coat the surface uniformly, leaving uncovered areas behind protrusions due to shadow effect, and this type of coating is too labor-intensive) and other techniques such as dip-coating do not work due to non-uniformity of the resulting film. Spin-coating cannot be applied due to viscosity of collagen material as well as un-coated zones behind the protrusions (same type of "shadow" effect as for brush-coating). Additionally, other techniques cannot guarantee a smooth surface with uniform layer thickness.

It is possible to use 3D printing (Kim, T. G., et al., 2010 "Microstructured scaffold coated with hydroxyapatite/collagen nanocomposite multilayer for enhanced osteogenic induction of human mesenchymal stem cells" *J Mater Chem* 20: 8927-8933), but this approach only works if coating is deposited at the same time as a material is built, e.g., when one layer of matrix is deposited, another layer of collagen is dispensed, then matrix is deposited again, then collagen again. In other words, use of 3D printing for surface coverage is not effective for two reasons: (1) in order to have complete coverage, the lines deposited by 3D printer should overlap, requiring significant time, and (2) in case of complex geometries, the 3D structures will not allow a printer head to get close enough to coat all the surface (it might work for flat surface with very small protrusions, but not for large protrusions, or curved surfaces).

It is possible to produce a negative mold of a surface, coat it with a biolayer of interest and press that mold to a 3D surface, but it is difficult to control uniformity and thickness of the layer. Additionally, this technique requires the production of molds for each surface to be coated.

SUMMARY

Some embodiments relate to an imprinter device comprising an array of adjacent applicators that are arranged so that longitudinal axes of each of the adjacent applicators are parallel to each other, wherein the applicators are configured to make contact with and conform to a surface of a three dimensional (3D) object.

In some embodiments, the applicators move independently of each other with respect to the surface of the object, and wherein the applicators are configured to apply a material over the object while in proximity to the surface of the object.

In some embodiments, the applicators are positioned in a pattern having an inter-applicator spacing of from 1-500 μm.

In some embodiments, the pattern is repeating grid pattern.

In some embodiments, the device is configured to apply a force to each of the applicators, wherein each of the applicators move perpendicularly towards the object along the longitudinal axes of the applicators, and wherein each of the applicators contact the surface of the object.

In some embodiments, the force applied to each applicator is provided by a device or system selected from the group consisting of a spring, a lever, a hydraulic system and an air pressure system.

In some embodiments, at a given time, at least one applicator may dispense a material while other applicators do not dispense the same material.

In some embodiments, each applicator in the array of applicators is connected to a different supply line configured to conduct said material through each applicator.

In some embodiments, each applicator is individually matched to a corresponding, dedicated pump.

In some embodiments, the array of applicators is configured so that different applicators can dispense different types of material to the object.

In some embodiments, the array contains at least 10 applicators.

In some embodiments, the applicators are selected from the group consisting of a rod having a solid end that contacts the surface of the object, a hollow nozzle and an applicator comprising a nozzle.

In some embodiments, the type, speed, rate, and/or pattern of the dispensed material is controlled by a computer.

Some embodiments relate to a method of conformal coating a surface of an object, the method comprising:
contacting an array of applicators with a surface of the object, wherein each applicator in the array of applicators conforms to a position of the surface of the object that the applicator contacts, and
dispensing a material from one or more applicators in the array of applicators and so that the material is applied to the surface of the object at position(s) contacted by the applicator(s).

In some methods, the material is dispensed while each applicator in the array of applicators is in contact with the surface of the object.

In some methods, different applicators in the array of applicators dispense different types of material.

In some methods, the material dispensed from the one or more applicators comprises a biological macromolecule and/or a biological cell.

In some methods, said biological macromolecule is selected from the group consisting of a extracellular matrix protein, a growth hormone and a collagen.

In some methods, the material dispensed from the one or more applicators does not contain a biological macromolecule and/or a biological living cell.

In some embodiments, cross-linkable polymers or resins are dispensed from individually-controlled applicators at different pressures and/or rates.

In some embodiments, a dispensed cross-linkable polymer or resin is cross-linked by an ambient UV source.

In some methods, the object is a biological scaffold.

In some methods, the object is a non-biological substrate.

In some methods, the material dispensed onto the object comprises a biological cell, and wherein the biological cell is cultured and grown in the object.

DETAILED DESCRIPTION OF CERTAIN EMBODIMENTS

Figure 1:
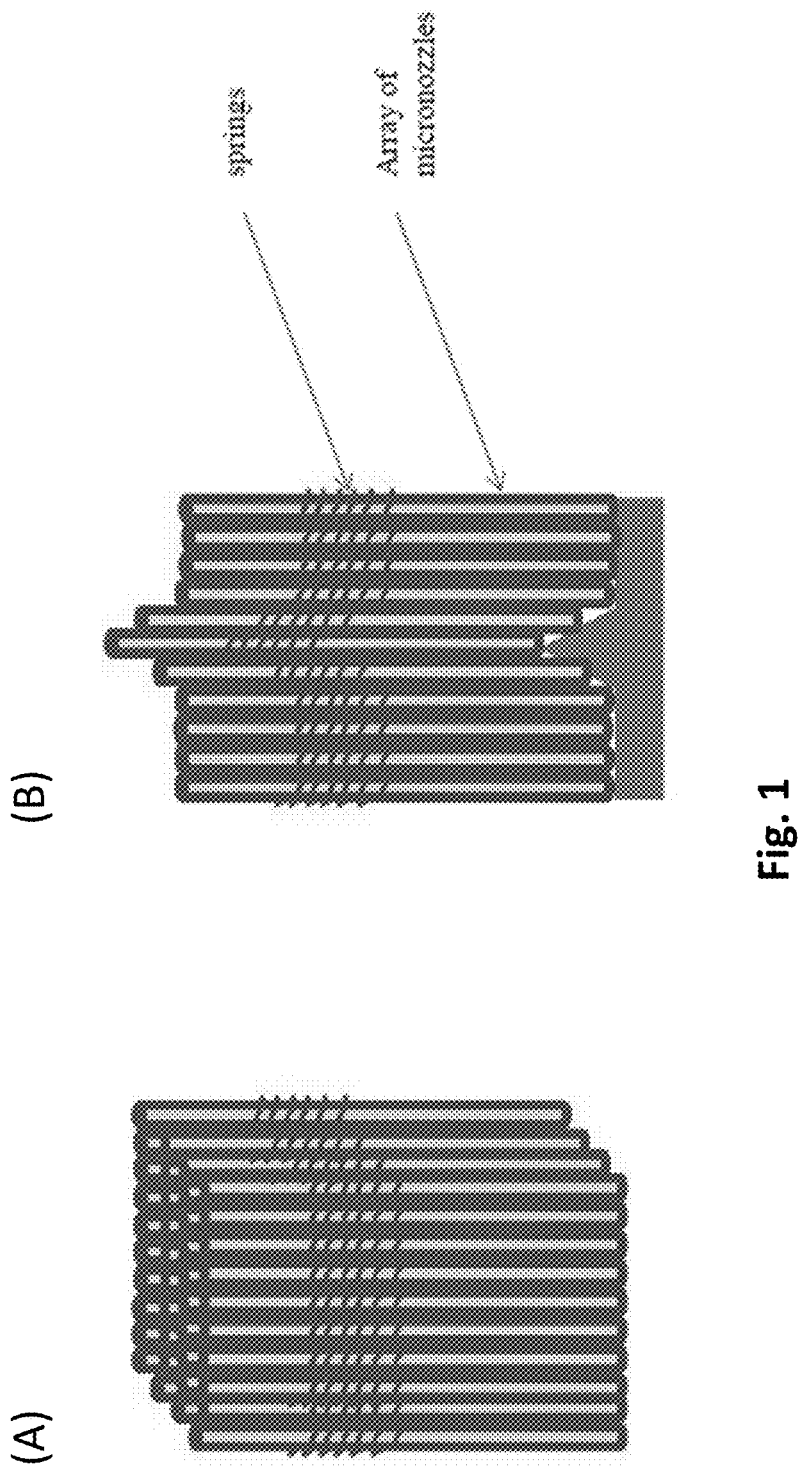
FIG. 1: Illustration of a conformal bioimprinter. (A) A bioimprinter including a dense array of spring-loaded nozzles. (B) When the bioimprinter is pressed down on a surface to be coated, the spring-loaded nozzles repeat the topology of the surface and the conformity depends on how small the micronozzles' diameter is and how dense the array is. When a biocoating media is ejected from the nozzles, it creates a conformal layer on the surface.

Some embodiments disclosed herein relate to a technique of conformal imprinting based on micronozzle array that allows conformal coating of arbitrarily complex 3D surfaces, without any need for producing negative molds or other labor-intensive and time-demanding technologies. This disclosure details a method of mask-free technology allowing for conformal coating of complex three-dimensional surfaces. The presented methodology allows conformal coating even for materials that cannot withstand shear stresses such as collagen laden with cells and thus this technique can be used for but not limited to bioimprinting of the cells and other biolayer onto arbitrary surfaces of tissue engineering construct or biomedical microdevices.

Some embodiments of the technology relate to a closely spaced array of spring-loaded micronozzles that, when pressed to the surface, will arrange according to the shape of the surface and make the contact at all points (with springs deflecting to various degrees to allow all the micronozzles of the array to make contact with the surface). Subsequently, the material is dispensed through the nozzle to coat the surface conformally. The pressure applied within each nozzle (for example, via displacement pump) can be self-contained for each nozzle for maximum control or the same pump can be used for all nozzles to extract the same amount of coating media from all the nozzles. The higher the density of the nozzle array, and the smaller the size of individual nozzles, the better the resolution of the system. In some embodiments, nozzles have individual pumps. Then patterning of a deposited layer is possible, where (similar to dot matrix printer) some nozzles will be on and will dispense media, some will be off and some nozzles might dispense different type(s) of media to be deposited simultaneously with other media or sequentially (after one pattern of media coat is deposited).

This disclosure allows ease of conformal coating of surfaces with various topologies, while not requiring specially prepared masks. A significant added benefit is that the media to be coated will not be exposed to large shear stresses.

Three dimensional microstructured scaffolds with precisely defined architectures have many promising features for tissue engineering applications, such as controllable porosity, optimal mechanical strength, and adjustable contour fitting to match a tissue defect site. We present a coating strategy to coat the surface of a microstructured scaffold. In some embodiments, the coating strategy has applications in tissue engineering.

Surface engineered biomaterials can present desirable physical, chemical, and biological functionalities, which favor cell adhesion, migration, and differentiation. In particular, tissue engineering scaffolds are frequently surface-modified with biologically active molecules to mimic the surface composition and topography of a natural extracellular matrix (ECM) structure. The consequent bifunctional cues on the surface play a critical role in regulating and accelerating tissue repair and regeneration processes. For example, hydroxyapatite (HAp), hyaluronic acid (HA), collagen, and several signaling molecules (e.g., bone morphogenetic protein and fibroblast growth factor) can be utilized for surface modification for the enhancement of an engineered tissue.

A conformal coating material is a thin coating that conforms to the contours of a substrate. For example, a conformal coating material may be applied at a thickness range of from 25-500 μm, 25-250 μm or 25-100 μm. Coating thicknesses may be about 5 μm, 10 μm, 20 μm, 30 μm, 40 μm, 50 μm, 60 μm, 60 μm, 80 μm, 90 μm, 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm or 500 μm. The methods disclosed herein provide a smooth surface coating having a uniform layer thickness.

Applicators and Coating Methods

In some embodiments, the applicators used in the disclosed imprinter devices may be configured as rods having solid ends configured to contact the surface of an object. A material applied to the solid end of the rods can be transferred to the surface of the object.

In another configuration, each applicator comprises a hollow conduit configured to conduct material through the applicator to a tip of the applicator, wherein the material is transferred to the surface of an object by the tip of the applicator.

In some embodiments, the applicator includes a nozzle. A nozzle is a device designed to control the direction or characteristics of a fluid flow (e.g., to increase velocity) as it exits an enclosed chamber or pipe. A nozzle may be a pipe or tube of varying cross sectional area, and it can be used to direct or modify the flow of a fluid (liquid or gas). Nozzles may be used to control the rate of flow, speed, direction, mass, shape, and/or the pressure of the stream that emerges from them. Nozzle velocity of a fluid increases inversely to a pressure energy of the nozzle.

In some embodiments, the applicators in an array of applicators are positioned in a repeating grid pattern having an inter-applicator spacing of from 25-500 μm. For example, the inter-applicator spacing may be about 25 μm, 10 μm, 20 μm, 30 μm, 40 μm, 50 μm, 60 μm, 60 μm, 80 μm, 90 μm, 100

μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm or 500 μm.

In some embodiments, an array of applicators may contains at least 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 150, 200, 250, 300 or more applicators.

In some embodiments, an applicator configured as a rod is used to contact transfer a material from a source onto a surface of an object. In other embodiments, an applicator contains a hollow conduit.

In other embodiments where an applicator that has a hollow conduit, a material is conducted through the applicator to a tip of the applicator, and the material is transferred to the surface of an object by the tip of the applicator, for example by flowing onto the surface of the object or by material dispersal mediated by a nozzle.

A coating material can be applied by from brushing, spraying and dipping. A conformal coating may contain a detectable reagent, e.g., a fluorescent dye, to aid in coating coverage inspection.

Spray application coating can be completed with a spray aerosol and is suitable for low and medium volume processing. A applicator nozzles may be used to spray a coating onto a substrate Coating Thickness Coating material may have a thickness of from 25-500 μm. For example a coating material may have a thickness of about 25 μm, 50 μm, 75 μm, 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm or 500 μm.

There are several methods for measurement of conformal coating thickness and they fall into two categories. These categories are wet film and dry film conformal coating measurements.

The wet film conformal coating thickness method ensures quality control while the coating is still wet. Applying too much coating can be expensive. Also, wet film measurements are useful for conformal coatings where the dry film thickness can only be measured destructively or over application of conformal coating could be problematic. The wet film gauges are applied to the wet conformal coating and the teeth indicate the thickness of the conformal coating. The dry film thickness can then be calculated from the measurement.

Dry film conformal coating thickness measurement may be done using a non-contact technique using eddy currents. For example, the system may work by placing the test head on the surface of the conformal coating, wherein the measurement is almost instantaneous and provides an immediate repeatable result for thickness measurement of conformal coating.

Test coupons can be used to measure a coating thickness, whether is it spraying or dipping, and can be kept as a physical record of the performance. Apply a coating to the test coupons at the same time as the substrate (e.g., a circuit board) provides a permanent measurement and an accurate guide to the coating thickness.

Thicker coatings or better applied coatings may be required when liquid water is present due to potential microscopic pinhole formation in the coating or when the coating material is too thin on the sharp edges of components due to poor application techniques. This is considered a defect and can be eliminated with appropriate steps and training.

Conformal Coating Selection

Biological Materials

Tissue engineering relates to the practice of combining scaffolds, cells, and biologically active molecules into functional tissues. A goal of tissue engineering is to assemble functional constructs that restore, maintain, or improve damaged tissues or whole organs. Artificial skin and cartilage are examples of engineered tissues that have been approved by the FDA.

Cells are the building blocks of tissue, and tissues are the basic unit of function in the body. Generally, groups of cells make and secrete their own support structures, called extracellular matrix. This matrix, or scaffold, does more than just support the cells; it also acts as a relay station for various signaling molecules. Thus, cells receive messages from many sources that become available from the local environment. Each signal can start a chain of responses that determine what happens to the cell. By understanding how individual cells respond to signals, interact with their environment, and organize into tissues and organisms, researchers have been able to manipulate these processes to mend damaged tissues or even create new ones.

The process often begins with building a scaffold from a wide set of possible sources, from proteins to plastics or metals (e.g., nitinol, stainless steel). Once scaffolds are created, cells with or without growth factors can be introduced. Under conducive conditions, a tissue develops.

Another method to create new tissue uses an existing scaffold. The cells of a donor organ are stripped and the remaining collagen scaffold is used to grow new tissue. This process has been used to bioengineer heart, liver, lung, and kidney tissue. This approach holds great promise for using scaffolding from human tissue discarded during surgery and combining it with a patient's own cells to make customized organs that would not be rejected by the immune system.

A scaffold can be formed to operate as a variety of tissues, such as a heart valve, or vascular graft. A biological matrix can include any desired number of layers, such a first layer (smooth muscle cells) formed directly on a scaffold, a second layer (fibroblast/myofibroblast cells) formed on the first layer, and a third layer (endothelial cells) formed on the second layer. Collagen may be provided as an additive to coat a scaffold to ensure development of an interconnected pore network. Growth of the tissue may be aided by the addition of growth factors. In addition, the culture media may be supplemented with additives, including, but not limited to, ascorbic acid to promote matrix production. Cytokines, including TGF-β1, may be added to the collagen gels in each layer to increase the rate of extracellular matrix production. For the biological part of the scaffold, any collagen type by itself or in mixture as well as the other biological scaffold such as fibrin or even synthetic scaffolds can be used. Growth factors depending on the target tissue and the cells that have been used can be different, such as vascular endothelial growth factor (VEGF) if endothelial progenitor cells are used instead of endothelial cells.

Non-Biological Materials

The selection of a conformal coating material should be considered carefully in relation to the application method. Conformal coating inspection is a critical factor in determining successful coating application and long term reliability of substrates, such as printed circuit boards. This can be done manually by the operator in an inspection booth by examining the substrate under white and UVA light or it can be done automatically by a conformal coating inspection system.

A particular type of coating, termed parylene, is applied with a vacuum deposition process versus a spray or needle application. Parylene is applied at the molecular level by a vacuum deposition process at ambient temperature. Film coatings from 0.100 to 76 μm can be easily applied in a single operation. An advantage of parylene coatings is that they cover hidden surfaces and other areas where spray and needle application are not possible. Coating thickness is very uniform, even on irregular surfaces. Some disadvantages are that: (i) any desired contact points such as battery contacts or connectors must be carefully covered with an air-tight mask to prevent the parylene from coating the contacts, (ii) it is a batch process and does not lend itself to high volume processing, and (iii) the cost per PCB can be highly prohibitive due to the capital investment costs and the cost per batch.

Many conformal coating chemistries are available, each having various strengths:

Acrylic coatings provide ease of rework, simple drying process, good moisture resistance, high Fluorescence level and ease of viscosity adjustment.

Epoxy coatings are useful to about 150° C. (302° F.), exhibit a harder durometer, show abrasion resistance, have a coefficient of thermal expansion (CTE) closer to epoxy Printed Circuit Board substrate, they have a higher Tg (Glass transition) and exhibit good dielectric properties.

Polyurethane coatings have good dielectric properties, good moisture resistance, solvent resistance, they have less reversion potential and they have good abrasion resistance.

Silicone coatings are stable over wide temperature range (in general, −40° C. to 200° C.), they are flexible and provide dampening and impact protection, they have good moisture resistance, high dielectric strength and low surface energy for better wetting Fluorinated or non Fluorinated coatings—Poly-Para-Xylylene (Parylene) show excellent uniformity regardless of part geometry, chemical inertness, minimal added mass and low outgassing, low environmental impact process, and low dielectric constants.

Amorphous Fluoropolymer coatings have low dielectric constants, high glass transition temperature, low surface energy, low water absorption and solvent resistance.

In some embodiments, cross-linkable polymers (resins) can be expressed from individually-controlled applicators at different pressures and/or rates.

In some embodiments, a cross-linkable polymer or resin may be cross-linked by an ambient UV source, wherein a 3D structure is created quickly. When viewed at high resolution, the 3D applied polymer may appear like an array of towers of different heights. This mode of polymer application is advantageous compared to current line-by-line (or layer-by-layer) additive manufacturing approaches, for example, leading to a higher throughput.

Example 1

Conformal Imprinter Prototype

Figure 2:
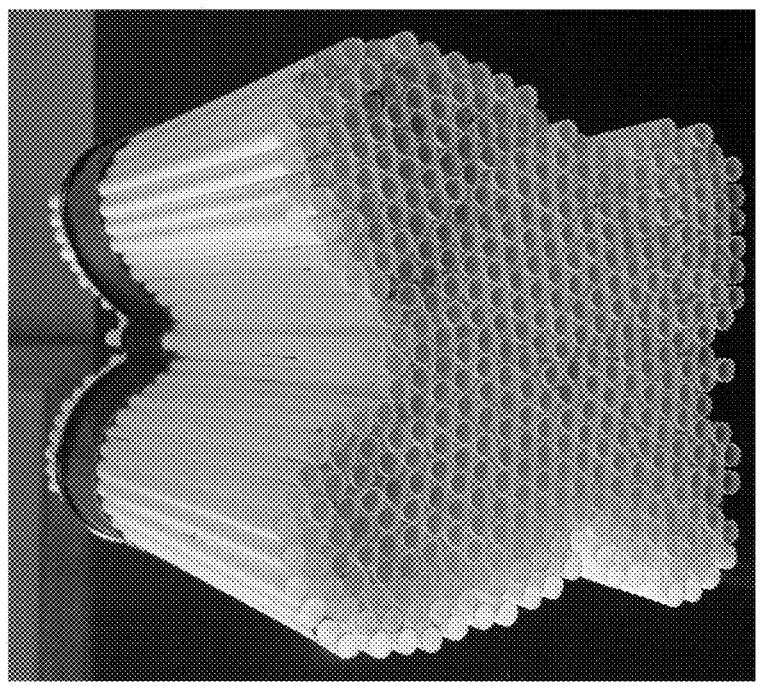
FIG. 2: A butterfly-shaped prototype conformal imprinter.

A first prototype conformal imprinter created by packing 1000 coffee straws (stirrers) with diameter of 3 mm in a box, dipping them in a rubberized paint (Plasti-dip) and placing it on a curved surface. A butterfly shape cookie mold was used to show this pattern (FIG. 2). Since the paint had low viscosity, the paint started to run and the pattern was not achieved.

Figure 3:
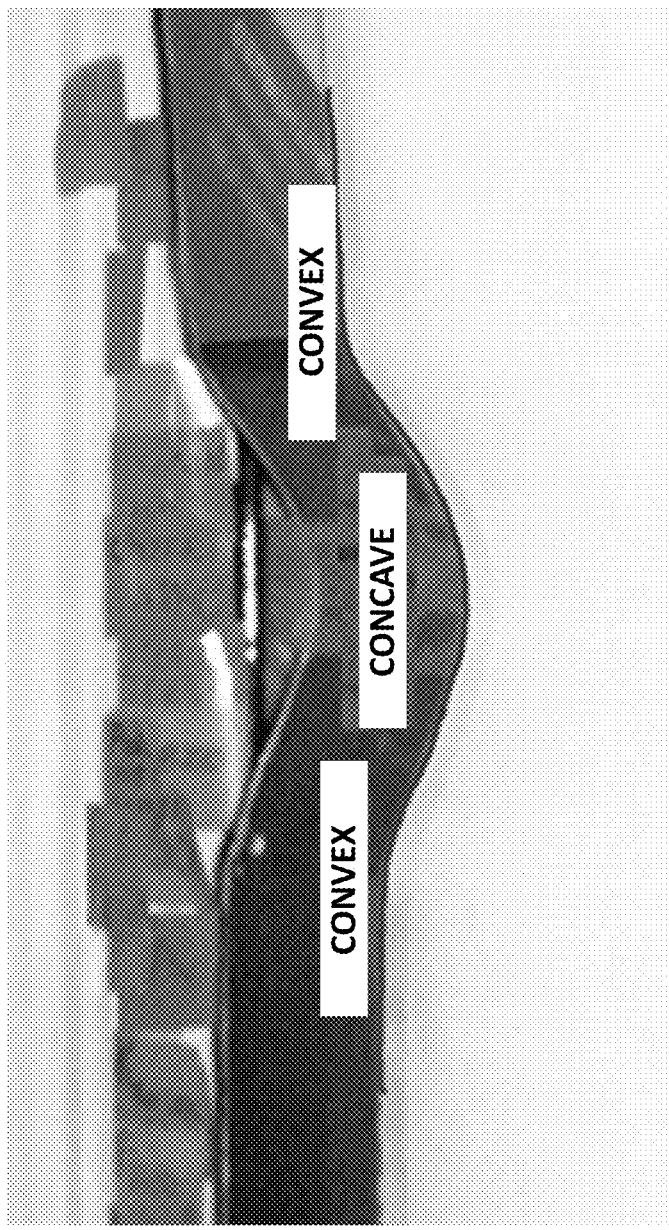
FIG. 3: Conformation of imprinter to a convex-concave-convex shape.

Another trial involved using the same setup, but instead of the rubberized paint, water-based acrylic paint was used. The butterfly mold was dipped in a container with paint and then was pressed on a book that was opened right in the middle and placed on a desk. This created a fore edge pattern on the pine of the book with two convex parts and a concave part in the middle (FIG. 3).

Figure 4:
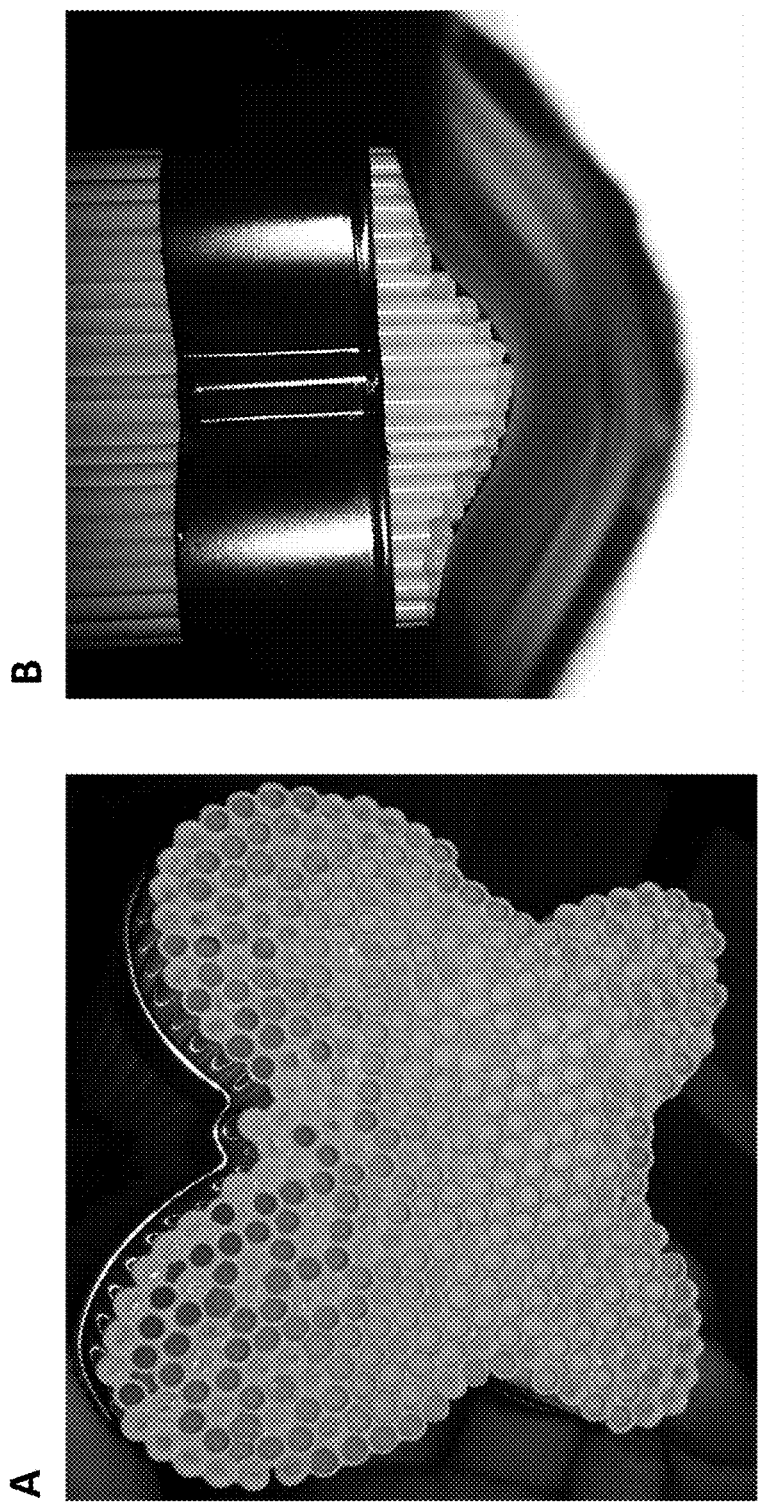
FIG. 4: Confirmation of imprinter to an irregular surface. (A) Butterfly-shaped conformal imprinter, (B) Conformal imprinter placed against an irregular surface.
Figure 5:
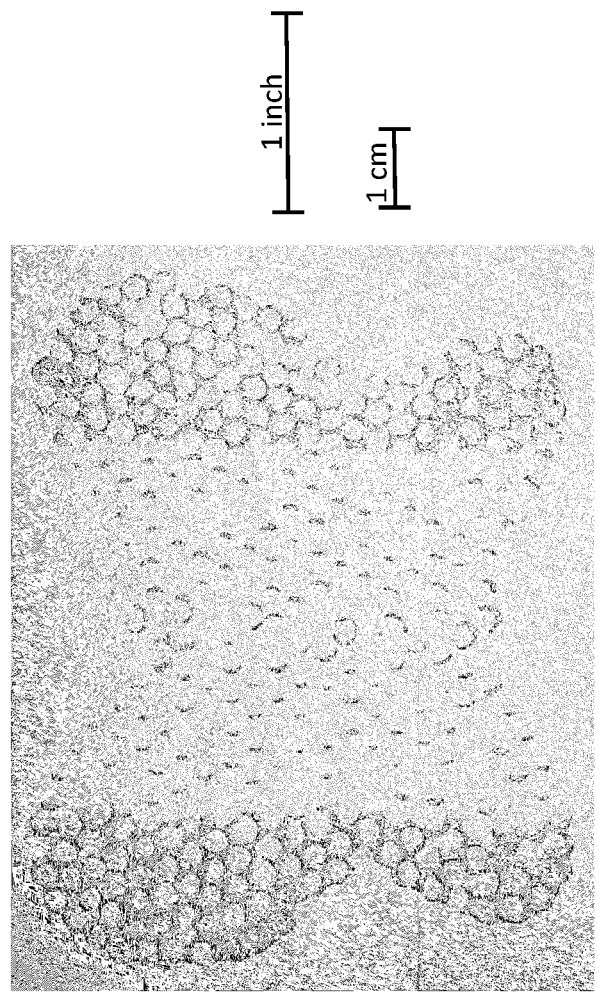
FIG. 5: Imprinted pattern created by imprinter on irregular surface.

FIG. 4 shows the dipped straws in the paint (top) and the mold placed on the hinge of the book (bottom), and FIG. 5 shows the created pattern on the paper.

Complete circular imprinting was only observed on surfaces that were flat (perpendicular to the longitudinal axis of the straws). Tilted surfaces (convex or concave) only created small dots since only the edge of the straws touched those planes. The full circular patterns in the middle of the butterfly indicate the flat surface right in the middle of the book, where the slop was zero.

Example 2

Imprinting on Paper Placed on Irregular Surfaces

Figure 6:
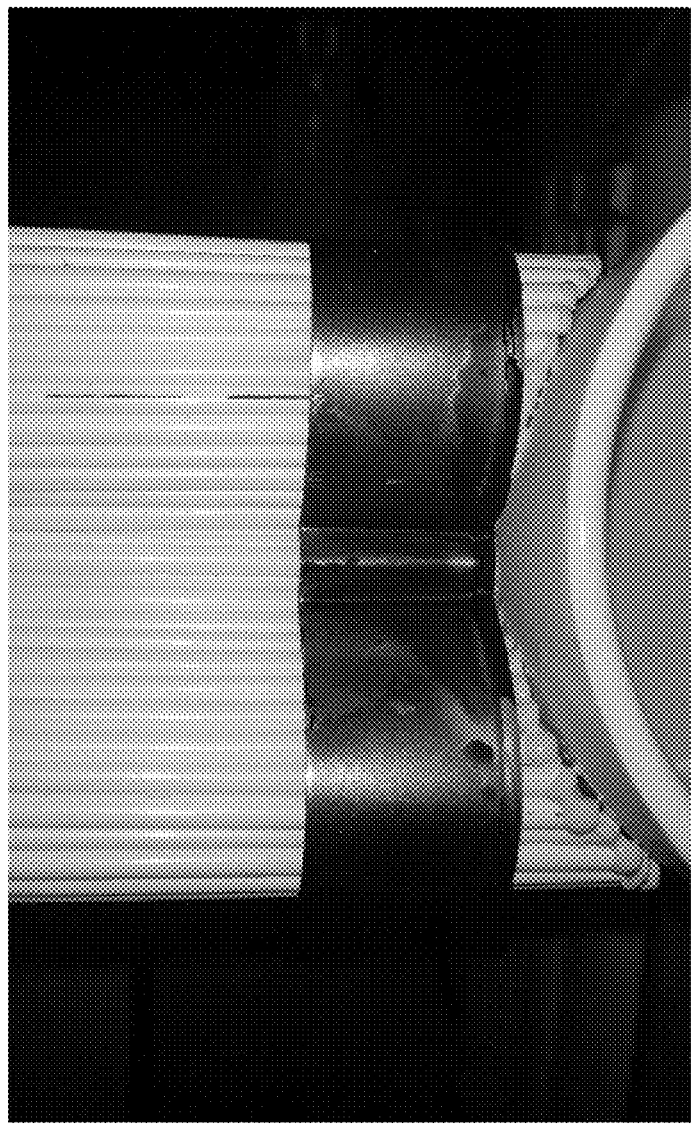
FIG. 6: Conformal imprinter placed against a convex shape.
Figure 7:
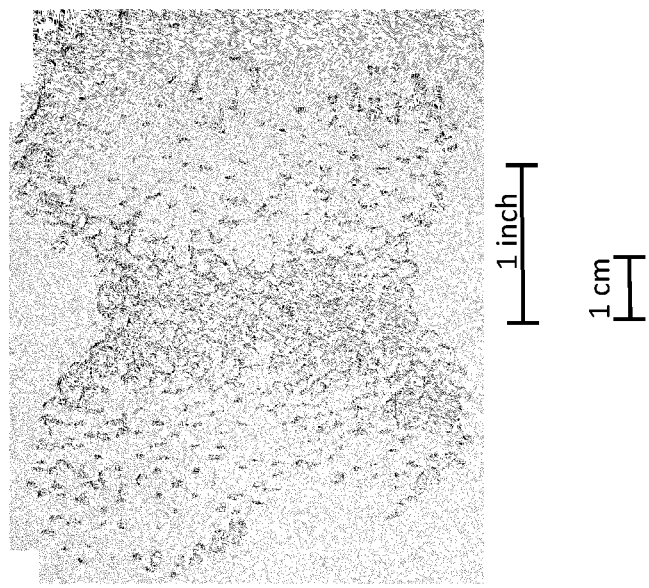
FIG. 7: Imprinted pattern created by imprinter on convex surface.
Figure 7:
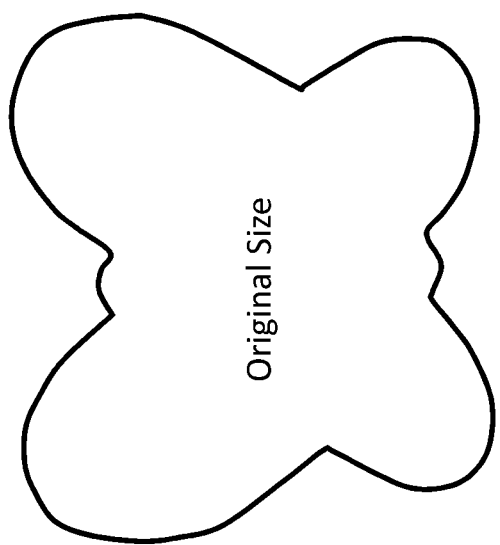

The next set of photos resulted from placing a piece of paper on the outside of a large mug. Paper was taped down to create a curved (convex) surface with no variation in the slope (FIG. 6). The imprinted pattern is shown in FIG. 7, comparing the original size of the imprinter compared to the imprinted image. Since the mold was placed perpendicular to the top side of the curvature, the paint was completely applied to the paper. However in the rest of the paper, the same dots started to appear due to the slope of the curvature. It should be noted that, if the mold was placed on the mug at an angle, we would have seen the complete circles where the longitudinal axis if the straws and the surface of the mug were perpendicular.

Example 3

Imprinting with Solid Rods

Figure 8:
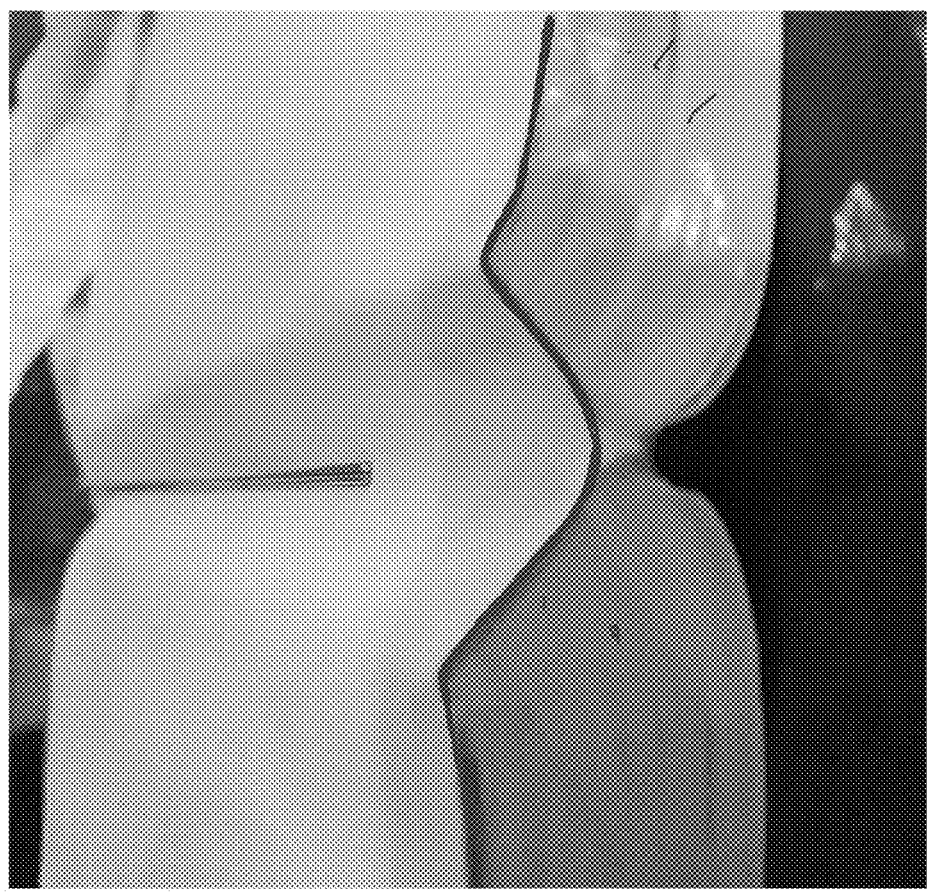
FIG. 8: Curved surface with highlighted curvature and transition.
Figure 9:
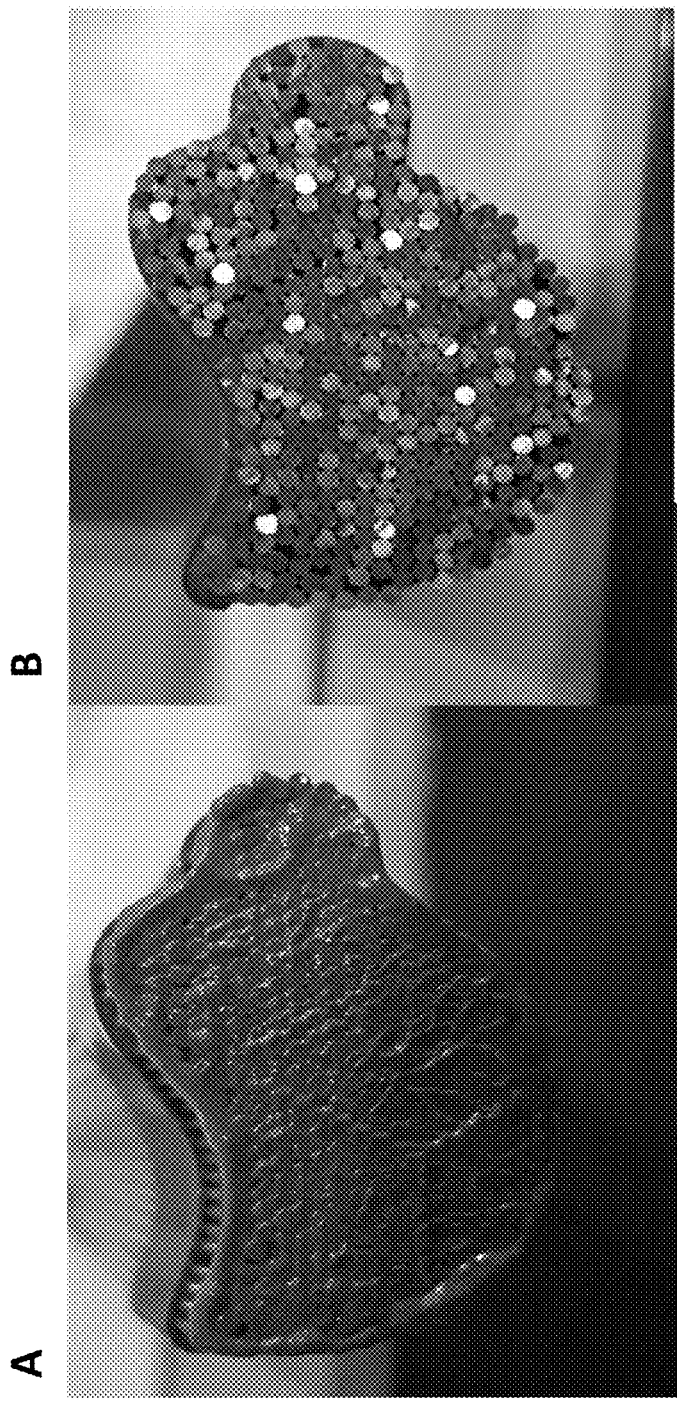
FIG. 9: Conformal imprinter, featuring brass rods.
Figure 10:
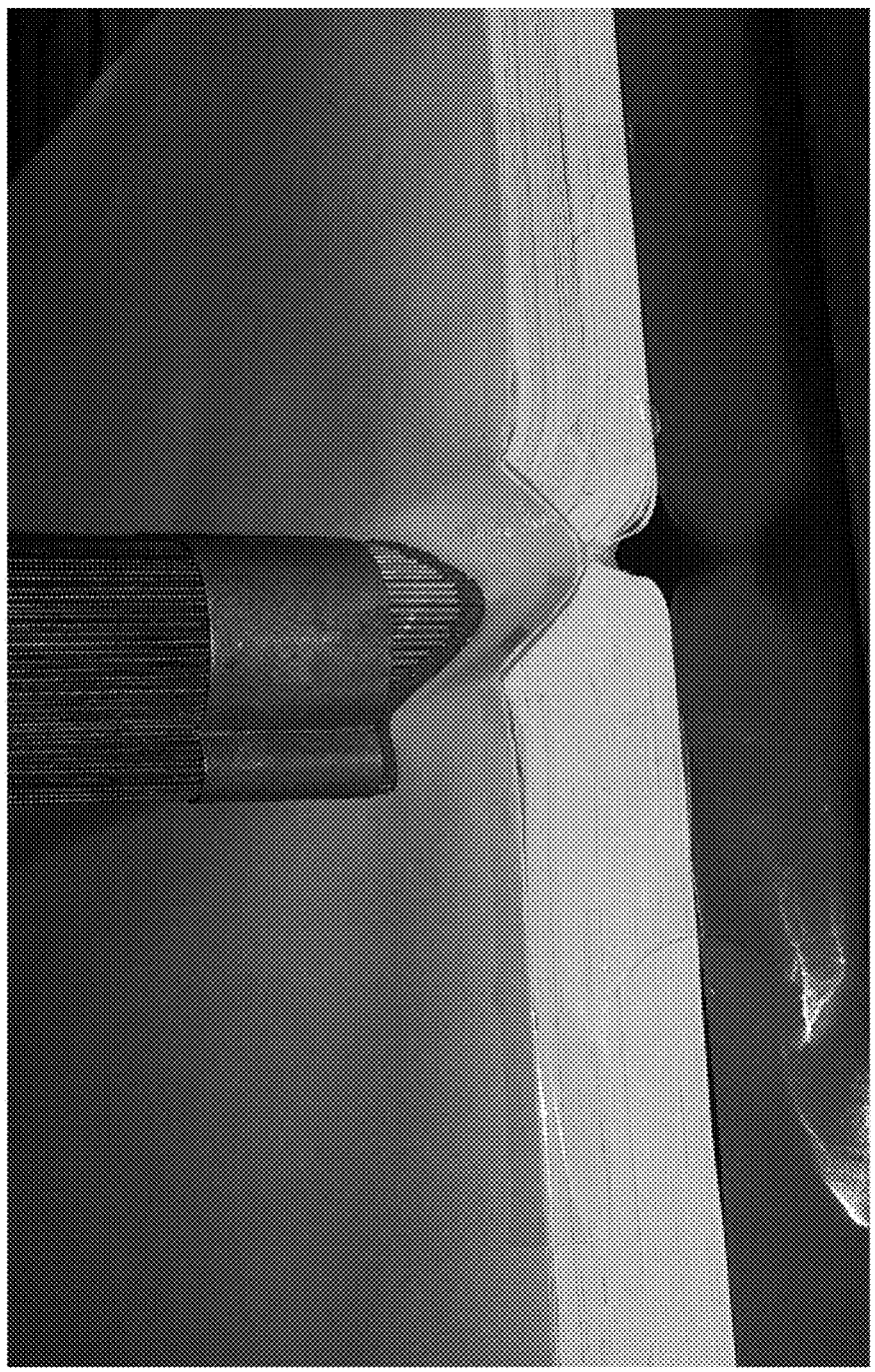
FIG. 10: Conformation of brass rod conformal printer to an irregular surface.
Figure 11:
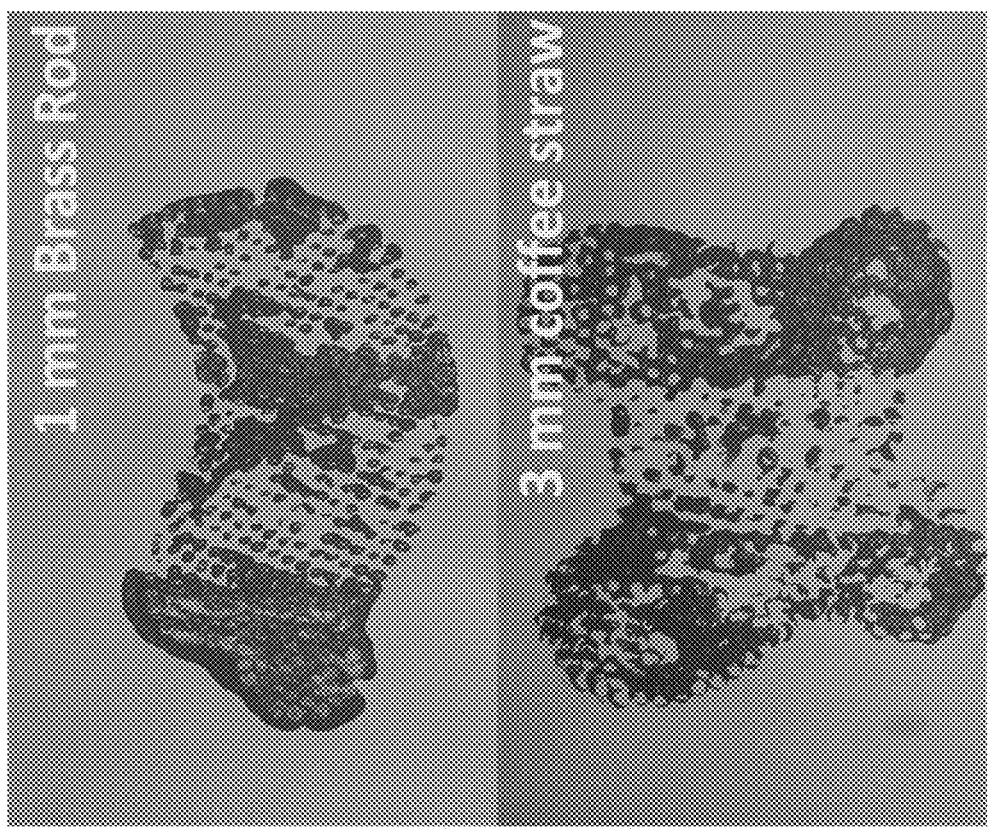
FIG. 11: Comparison of imprinted patterns. (A) Brass rods (1 mm), (B) plastic straws (3 mm).

Analysis of imprinting by solid brass rods was tested. Brass rods were chosen that were ⅓ of the diameter of the original coffee straws that were used. Due to smaller size of the rods, a smaller mold was used to hold the rods. The same directions were used for this setup to compare with the previous setup. FIG. 8 shows the hinge of the book with red line showing the curvatures and transition. FIG. 9 shows the conformal imprinter made of brass rods before (B) and after (A) application of paint to the tips of the rods. FIG. 10 shows the brass rod imprinter contacting the hinge of a book, representing an irregular surface with convex and concave surfaces. FIG. 11 shows a comparison of imprinted images, contrasting images created by a conformal imprinter made of 1 mm brass rods (A) and a conformal imprinter made with 3 mm coffee straws.

Figure 12:
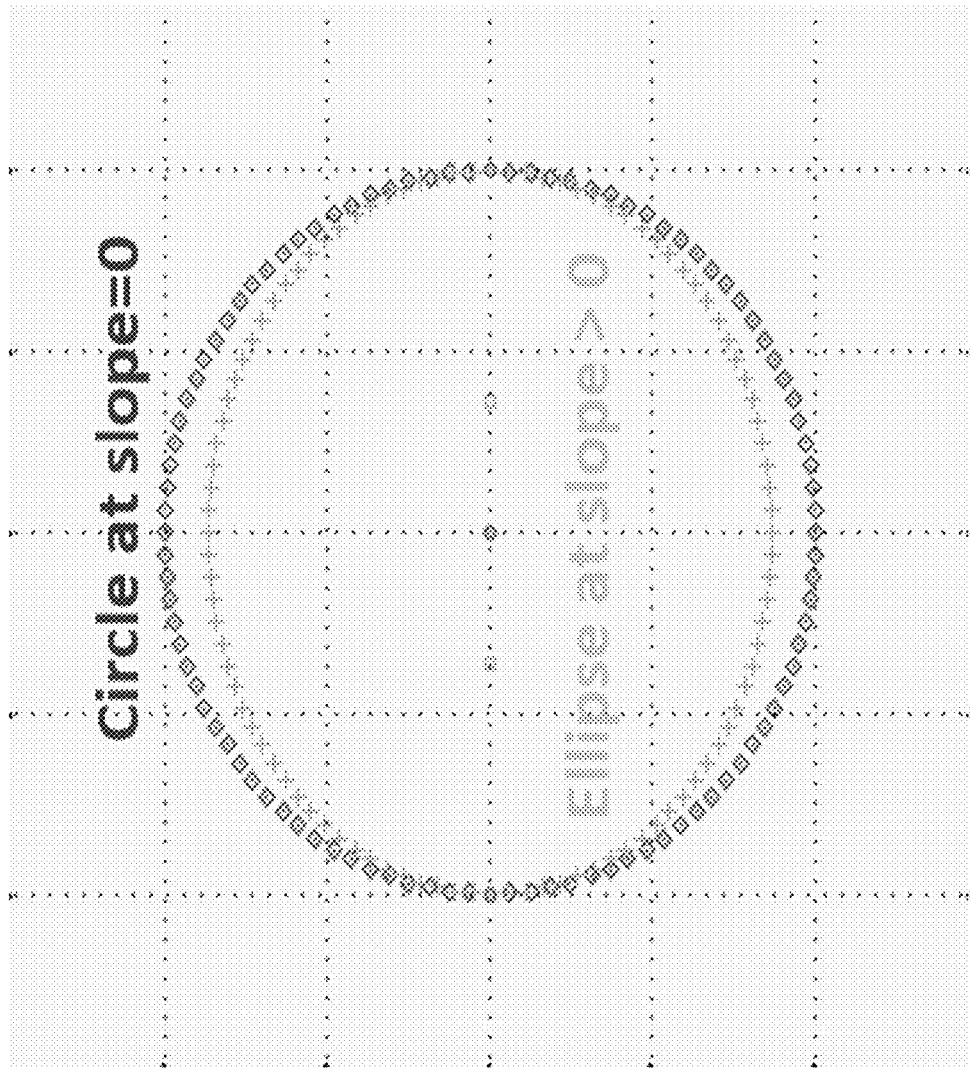
FIG. 12: Imprinting of circular and elliptical patterns. Circles (◊) imprinted at a surface slope of 0 and elliptical patterns (+) at a surface slope >0.
Figure 13:
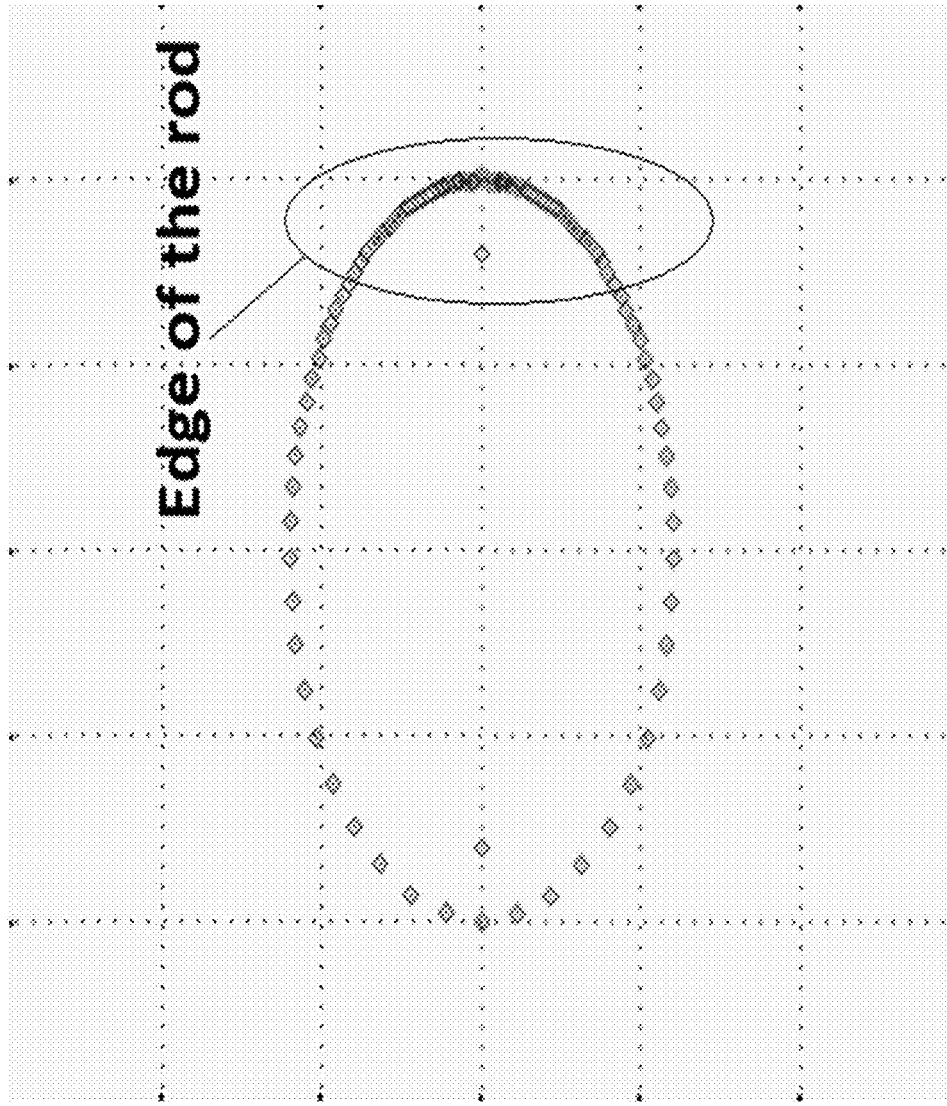
FIG. 13: Concentration of paint at the edges a rods, demonstrating a high concentration of paint on the edges (right) compared a lower concentration of paint at positions away from the edges of rods (left).

Equivalent results were achieved when the size of the straws/rods was decreased. This is expected since the edge of the rods does not allow them to move further down on a surface, leaving the paint on unexposed portions of the tips of the straws/rods untouched. However, on surfaces that came into perpendicular contact with the longitudinal axes of rods, a circular pattern was applied to the paper. To prevent this, a piece of cloth can be used, allowing each rod to move further down on a sloped surface, so that the edges of the rods do not create limitations on the sloped surfaces. A disadvantage to this approach is that surfaces with slopes of greater that zero will not show a circular pattern, but will start to show an ellipse (FIG. 12), consistent with the results obtained with a surface with a slope. Starting with a perfect circle, if a surface is tilted (creating slope) on one axis of this circle, an ellipse is created. Increasing the slope increases the length of the ellipse, keeping the minor axis the same. FIG. 13 shows a high concentration of paint on the right (corresponding to the edges of rods) and lower concentration on the left, corresponding to the non-edge regions of the rod tips. This is consistent with our experimental result on a surface having a slope.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. An imprinter device comprising an array of adjacent applicators that are arranged so that longitudinal axes of each of the adjacent applicators are parallel to each other, wherein the applicators are configured to make contact with and conform to a surface of a three dimensional (3D) object, and wherein the applicators are configured to move independently of each other with respect to the surface of the object.

2. The imprinter device according to claim 1, wherein the applicators are configured to apply a material to the object while in proximity to the surface of the object.

3. The imprinter device according to claim 1, wherein the applicators are positioned in a pattern having an inter-applicator spacing of from 1-500 µm.

4. The imprinter device according to claim 3, wherein the pattern is repeating grid pattern.

5. The imprinter device according to claim 1, wherein the device is configured to apply a force to each of the applicators, wherein each of the applicators move perpendicularly towards the object along the longitudinal axes of the applicators, and wherein each of the applicators contact the surface of the object.

6. The imprinter device according to claim 5, wherein the force applied to each applicator is provided by a device or system selected from the group consisting of a spring, a lever, a hydraulic system and an air pressure system.

7. The imprinter device according to claim 1, wherein, at a given time, at least one applicator may dispense a material while other applicators do not dispense the same material.

8. The imprinter device according to claim 1, wherein each applicator in the array of applicators is connected to a different supply line configured to conduct said material through each applicator.

9. The imprinter device according to claim 8, wherein each applicator is individually matched to a corresponding, dedicated pump.

10. The imprinter device according to claim 1, wherein the array of applicators is configured so that different applicators can dispense different types of material to the object.

11. The imprinter device according to claim 1, wherein the array contains at least 10 applicators.

12. The imprinter device according to claim 1, wherein the applicators are selected from the group consisting of a rod having a solid end that contacts the surface of the object, a hollow nozzle and an applicator comprising a nozzle.

13. The imprinter device according to claim 1, wherein the type, speed, rate, and/or pattern of the dispensed material is controlled by a computer.

14. A method of conformal coating a surface of an object, the method comprising
    contacting the imprinter according to claim 1 with a surface of the object, wherein each applicator in the array of applicators conforms to a position of the surface of the object that the applicator contacts, and
    dispensing a material from one or more applicators in the array of applicators and so that the material is applied to the surface of the object at position(s) contacted by the applicator(s).

15. The method according to claim 14, wherein the material is dispensed while each applicator in the array of applicators is in contact with the surface of the object.

16. The method according to claim 14, wherein different applicators in the array of applicators dispense different types of material.

17. The method according to claim 14, wherein the material dispensed from the one or more applicators comprises a biological macromolecule and/or a biological cell.

18. The method according to claim 17, wherein said biological macromolecule is selected from the group consisting of a extracellular matrix protein, a growth hormone and a collagen.

19. The method according to claim 17, wherein the material dispensed onto the object comprises a biological cell, and wherein the biological cell is cultured and grown in the object.

20. The method according to claim 14 wherein the material dispensed from the one or more applicators does not contain a biological macromolecule and/or a biological living cell.

21. The method according to claim 20, wherein cross-linkable polymers or resins are dispensed from individually-controlled applicators at different pressures and/or rates.

22. The method according to claim 20, wherein a dispensed cross-linkable polymer or resin is cross-linked by an ambient UV source.

23. The method according to claim 14, wherein the object is a biological scaffold.

24. The method of claim 14, wherein the object is a non-biological substrate.

* * * * *